United States Patent
Khan et al.

(10) Patent No.: US 7,560,433 B2
(45) Date of Patent: *Jul. 14, 2009

(54) TREATMENT OF MULTIPLE SCLEROSIS (MS)

(75) Inventors: Nisar Ahmed Khan, Rotterdam (NL); Robbert Benner, Barendrecht (NL)

(73) Assignee: Biotempt B.V., Koekange (NL)

( * ) Notice: Subject to any disclaimer, the term of this patent is extended or adjusted under 35 U.S.C. 154(b) by 475 days.

This patent is subject to a terminal disclaimer.

(21) Appl. No.: 10/409,630

(22) Filed: Apr. 8, 2003

(65) Prior Publication Data

US 2003/0215434 A1 Nov. 20, 2003

Related U.S. Application Data

(63) Continuation-in-part of application No. 10/028,075, filed on Dec. 21, 2001.

(51) Int. Cl.
  *A61K 38/00* (2006.01)
  *A61K 38/02* (2006.01)
  *A61K 38/07* (2006.01)
  *A61K 38/24* (2006.01)
(52) U.S. Cl. .......................................... 514/18; 514/2
(58) Field of Classification Search ........................ None
See application file for complete search history.

(56) References Cited

U.S. PATENT DOCUMENTS

| | | | |
|---|---|---|---|
| 4,330,466 A | 5/1982 | Yanaihara et al. | |
| 4,427,660 A | 1/1984 | Schiffman et al. | |
| 4,571,336 A | 2/1986 | Houck et al. | |
| 4,753,965 A * | 6/1988 | Stemerick et al. | 514/647 |
| 4,855,285 A | 8/1989 | Stevens | |
| 4,977,244 A | 12/1990 | Muchmore et al. | |
| 5,002,961 A | 3/1991 | Dage et al. | |
| 5,010,175 A | 4/1991 | Rutter et al. | |
| 5,055,447 A | 10/1991 | Palladino et al. | |
| 5,223,397 A | 6/1993 | Pouletty | |
| 5,308,834 A | 5/1994 | Scott et al. | |
| 5,380,668 A | 1/1995 | Herron | |
| 5,436,270 A | 7/1995 | Wang | |
| 5,677,275 A | 10/1997 | Lunardi-Iskandar et al. | |
| 5,700,781 A | 12/1997 | Harris | |
| 5,801,193 A | 9/1998 | Ojo-Amaize et al. | |
| 5,837,478 A | 11/1998 | Gallatin et al. | |
| 5,851,997 A | 12/1998 | Harris | |
| 5,854,004 A | 12/1998 | Czernilofsky et al. | |
| 5,856,440 A | 1/1999 | Wang | |
| 5,877,148 A | 3/1999 | Lunardi-Iskandar et al. | |
| 5,942,494 A | 8/1999 | Ginsberg et al. | |
| 5,958,413 A | 9/1999 | Anagnostopulos et al. | |
| 5,966,712 A | 10/1999 | Sabatini et al. | |
| 5,968,513 A | 10/1999 | Gallo et al. | |
| 5,972,924 A | 10/1999 | Keep et al. | |
| 5,981,486 A | 11/1999 | Matsushima et al. | |
| 5,994,126 A | 11/1999 | Steinman et al. | |
| 5,997,871 A | 12/1999 | Gallo et al. | |
| 6,022,696 A | 2/2000 | Harding et al. | |
| 6,051,596 A * | 4/2000 | Badger | 514/409 |
| 6,075,150 A | 6/2000 | Wang et al. | |
| 6,086,918 A | 7/2000 | Stern et al. | |
| 6,150,500 A | 11/2000 | Salerno | |
| 6,207,145 B1 | 3/2001 | Tovey | |
| 6,235,281 B1 | 5/2001 | Stenzel et al. | |
| 6,278,794 B1 | 8/2001 | Parekh et al. | |
| 6,309,822 B1 | 10/2001 | Fodor et al. | |
| 6,310,041 B1 | 10/2001 | Haddox et al. | |
| 6,319,504 B1 | 11/2001 | Gallo et al. | |
| 6,329,573 B1 | 12/2001 | Lightfoot et al. | |
| 6,361,992 B1 | 3/2002 | Szkudlinski et al. | |
| 6,379,970 B1 | 4/2002 | Liebler et al. | |
| 6,416,959 B1 | 7/2002 | Giuliano et al. | |
| 6,489,296 B1 | 12/2002 | Grinnell et al. | |
| 6,507,788 B1 | 1/2003 | Camara y Ferrer et al. | |
| 6,518,021 B1 | 2/2003 | Thastrup et al. | |
| 6,539,102 B1 | 3/2003 | Anderson et al. | |

(Continued)

FOREIGN PATENT DOCUMENTS

DE          3715662          11/1987

(Continued)

OTHER PUBLICATIONS

Emmel et al, Science, Dec. 22, 1989, vol. 246, pp. 1617-1620.*
McDonald et al. Interleukin-15 (IL-15) induces NF-kappaB activation and IL-8 production in human neutrophils. Blood. vol. 92, No. 12, pp. 4828-4835, Dec. 1998.*
Smith et al. Recent developments in drug therapy for multiple sclerosis. Mult Scler. vol. 5, No. 2, pp. 110-120, Apr. 1999.*
Flores et al. NFkappaB and AP-1 DNA binding activity in patients with multiple sclerosis. J Neuroimmunol. vol. 135, No. 1-2, pp. 141-147, Feb. 2003.*
Clerici et al. Single-cell analysis of cytokine production shows different immune profiles in multiple sclerosis patients with active or quiescent disease. Journal of Neuroimmunology, vol. 121, pp. 88-101, 2001.*

(Continued)

*Primary Examiner*—Christopher S. F. Low
*Assistant Examiner*—Jennifer Dunston
(74) *Attorney, Agent, or Firm*—TraskBritt

(57) ABSTRACT

The invention relates to the treatment multiple sclerosis, and in particular to the treatment of the inflammatory injury seen in the progressive stages in the disease such as seen with the recurrent upsurges of acute disease, classically known as "relapses" or "exacerbations" or "relapsing/remitting" disease seen in multiple sclerosis. The invention provides a method for modulating a relapsing/remitting disease in a subject suffering therefrom involving providing the subject with a gene-regulatory peptide or functional analogue thereof. Furthermore, the invention provides the use of an NF-κB down-regulating peptide or functional analogue thereof for the production of a pharmaceutical composition for the treatment of relapsing/remitting disease as seen with multiple sclerosis.

1 Claim, No Drawings

U.S. PATENT DOCUMENTS

| | | | |
|---|---|---|---|
| 6,583,109 B1 * | 6/2003 | Gallo et al. ............... | 514/2 |
| 6,586,403 B1 | 7/2003 | Mathison et al. | |
| 6,596,688 B1 | 7/2003 | Gallo et al. | |
| 6,620,416 B1 | 9/2003 | Gallo et al. | |
| 6,630,138 B2 | 10/2003 | Gerlitz et al. | |
| 6,652,860 B1 | 11/2003 | Singh et al. | |
| 6,699,656 B2 | 3/2004 | Gallo et al. | |
| 6,711,563 B1 | 3/2004 | Koskas | |
| 6,727,227 B1 | 4/2004 | Khavinson | |
| 6,783,757 B2 | 8/2004 | Brudnak | |
| 6,831,057 B2 | 12/2004 | Baldwin et al. | |
| 6,844,315 B2 | 1/2005 | Khan et al. | |
| 6,852,697 B1 | 2/2005 | Mathison et al. | |
| 6,921,751 B1 | 7/2005 | Khan et al. | |
| 7,094,760 B2 | 8/2006 | Mathison et al. | |
| 7,135,286 B2 | 11/2006 | Margus et al. | |
| 7,175,679 B2 | 2/2007 | Khan et al. | |
| 7,358,330 B2 | 4/2008 | Khan et al. | |
| 7,365,155 B2 | 4/2008 | Khan et al. | |
| 7,368,535 B2 | 5/2008 | Gorczynski et al. | |
| 2002/0041871 A1 | 4/2002 | Brudnak | |
| 2002/0064501 A1 | 5/2002 | Khan et al. | |
| 2002/0147306 A1 | 10/2002 | Lin et al. | |
| 2002/0183255 A1 | 12/2002 | Lipton et al. | |
| 2003/0003545 A1 | 1/2003 | Ebner et al. | |
| 2003/0017203 A1 | 1/2003 | Crotts et al. | |
| 2003/0049273 A1 | 3/2003 | Gallo et al. | |
| 2003/0113733 A1 | 6/2003 | Khan et al. | |
| 2003/0119720 A1 | 6/2003 | Khan et al. | |
| 2003/0148955 A1 | 8/2003 | Pluenneke | |
| 2003/0166556 A1 | 9/2003 | Khan et al. | |
| 2003/0186244 A1 | 10/2003 | Margus et al. | |
| 2003/0215434 A1 | 11/2003 | Khan et al. | |
| 2003/0219425 A1 | 11/2003 | Khan et al. | |
| 2003/0220257 A1 | 11/2003 | Benner et al. | |
| 2003/0220258 A1 | 11/2003 | Benner et al. | |
| 2003/0220259 A1 | 11/2003 | Benner et al. | |
| 2003/0220260 A1 | 11/2003 | Khan et al. | |
| 2003/0220261 A1 | 11/2003 | Khan et al. | |
| 2003/0224995 A1 | 12/2003 | Khan et al. | |
| 2004/0013661 A1 | 1/2004 | Wensvoort et al. | |
| 2004/0208885 A1 | 10/2004 | Khan et al. | |
| 2005/0037430 A1 | 2/2005 | Khan et al. | |
| 2005/0214943 A1 | 9/2005 | Khan et al. | |
| 2005/0227925 A1 | 10/2005 | Benner et al. | |
| 2006/0111292 A1 | 5/2006 | Khan et al. | |
| 2006/0142205 A1 | 6/2006 | Benner et al. | |
| 2006/0275255 A1 | 12/2006 | Gudkov | |
| 2007/0197447 A1 | 8/2007 | Khan et al. | |
| 2008/0076714 A1 | 3/2008 | Khan et al. | |
| 2008/0171094 A1 | 7/2008 | Benner et al. | |
| 2008/0176243 A1 | 7/2008 | Khan et al. | |
| 2008/0194489 A1 | 8/2008 | Khan et al. | |
| 2008/0242618 A1 | 10/2008 | Khan et al. | |
| 2008/0242837 A1 | 10/2008 | Khan et al. | |

FOREIGN PATENT DOCUMENTS

| | | |
|---|---|---|
| DE | 19953339 | 5/2001 |
| EP | 0 572 688 | 5/1997 |
| EP | 1 138 692 A1 | 10/2001 |
| EP | 1 300 418 | 4/2003 |
| EP | 1 224 212 B1 | 7/2003 |
| EP | 1 466 612 A1 | 10/2004 |
| FR | 2 706 772 | 12/1994 |
| GB | 2 194 886 A | 3/1988 |
| WO | WO 9220795 A1 | 11/1992 |
| WO | 96/04008 | 2/1996 |
| WO | WO 96/33218 | 10/1996 |
| WO | 97/49373 | 12/1997 |
| WO | 97/49418 | 12/1997 |
| WO | 97/49432 | 12/1997 |
| WO | WO 97/49721 | 12/1997 |
| WO | WO 98/06742 | 2/1998 |
| WO | WO 98/35691 | 8/1998 |
| WO | WO 9834631 A1 * | 8/1998 |
| WO | WO 99/31227 | 6/1999 |
| WO | WO 99/59617 | 11/1999 |
| WO | WO 9959617 A2 * | 11/1999 |
| WO | WO 00/17348 | 3/2000 |
| WO | WO 01/10907 A2 | 2/2001 |
| WO | WO 01/11048 A2 | 2/2001 |
| WO | WO 0110457 A2 | 2/2001 |
| WO | WO 01/29067 | 4/2001 |
| WO | WO 01/29069 A1 | 4/2001 |
| WO | WO 01/32196 A1 | 5/2001 |
| WO | WO 01/36454 A1 | 5/2001 |
| WO | WO 01/51508 A1 | 7/2001 |
| WO | WO 01/68113 A1 | 9/2001 |
| WO | WO 01/72831 | 10/2001 |
| WO | WO 01/83554 A2 | 11/2001 |
| WO | WO 02/085117 | 10/2002 |
| WO | WO 03/029292 A2 | 4/2003 |
| WO | WO 2006/069198 A1 | 6/2006 |

OTHER PUBLICATIONS

International Search Report, International Application No. PCT/NL02/00639, mailed Aug. 4, 2003 (8 pages).

Christman et al., Nuclear factor kappaB: a pivotal role in the systemic inflammatory response syndrome and new target for therapy, Intens Care Med, 1998, pp. 1131-1138, vol. 24.

Jyonouchi et al., Proinflammatory and regulatory cytokine production associated with innate and adaptive immune responses in children with autism spectrum disorders and developmental regression, J Neuroim., 2001, pp. 170-179, vol. 120.

Kanungo et al., Advanced Maturation of Heteropneustes Fossilis (Bloch) by Oral Administration of Human Chorionic Gonadotropin, J. Adv. Zool., 1999, pp. 1-5, vol. 20.

Patil, A., et al., "The Study of the Effect of Human Chorionic Gonadotrophic (HCG) Hormone on the Survival of Adrenal Medulla Transplant in Brain. Preliminary Study," 87 Acta Neurochir (Wien) 76-78 (1987).

Rohrig et al., Growth-stimulating Influence of Human Chorionic Gonadotropin (hCG) on Plasmodium falciparum in vitro, Zentralblatt Bakt, 1999, pp. 89-99, vol. 289.

Slater, Lewis M., et al., "Decreased Mortality of Murine Graft-Versus-Host Disease by Human Chorionic gonadotropin,"23(1) Transplantation 103-104 (Jan. 1977).

Tak et al., NF-kappaB: a key role in inflammatory diseases, J Clin Invest., 2001, pp. 7-11, vol. 107.

Tan et al., The role of activation of nuclear factor-kappa B of rat brain in the pathogenesis of experimental allergic encephalomyelitis, Acta Physiol Sinica, 2003, pp. 58-64, vol. 55.

Tovey et al., Mucosal Cytokine Therapy: Marked Antiviral and Antitumor Activity, J. Interferon Cytokine Res., 1999, pp. 911-921, vol. 19.

Albini, A., et al., "Old drugs as novel angiogenesis inhibitors: Preclinical studies with NAC, hCG, EGCG and somatostatin," 17 Clinical & Experimental Metastasis 739 (1999).

Blackwell, Timothy S., et al., "The Role of Nuclear Factor-kB in Cytokine Gene Regulation," 17 Am. J. Respir. Cell Mol. Biol. 3-9 (1997).

Keller, S., et al., "Human Chorionic Gonadotropin (hCG) Is a Potent Angiogenic Factor for Uterine Endothelial Cells in Vitro," 20(5-6) Placenta, p. A37 (Jul. 1999).

Khan, Nisar A., et al., "Inhibition of Diabetes in NOD Mice by Human Pregnancy Factor," 62(12) Human Immunology 1315-1323 (Dec. 2001).

Khan, Nisar A., et al., "Inhibition of Septic Shock in Mice by an Oligopeptide From the β-Chain of Human Chorionic Gonadotrophin Hormone," 63(1) Human Immunology 1-7 (Jan. 2002).

Muchmore et al., Immunoregulatory Properties of Fractions from Human Pregnancy Urine: Evidence that Human Chorionic Gonadotropin is not Responsible, The Journal of Immunology, Mar. 1997, pp. 881-886, vol. 118, No. 3.

Muchmore et al., Purification and Characterization of a Mannose-Containing Disaccharide Obtained from Human Pregnancy Urine, Journal of Experimental Medicine, Dec. 1984, pp. 1672-1685, vol. 160.

Wulczyn, F. Gregory, et al., "The NF-kB/Rel and IkB gene families: mediators of immune response and inflammation," 74(12) J. Mol. Med. 749-769 (1996).

Yamamoto, Y., et al., "Role of the NF-kB Pathway in the Pathogenesis of Human Disease States," 1(3) Current Molecular Medicine 287-296 (Jul. 2001).

Samaniego et al., Induction of Programmed Cell Death in Kaposi's Sarcoma Cells by Preparations of Human Chorionic Gonadotropin, Journal of the National Cancer Institute, Jan. 20, 1999, pp. 135-143, vol. 91, No. 2.

PCT International Search Report, PCT/EP2005/003707, dated Jul. 5, 2005.

Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.

Ivanov et al., "Hemoglobin as a Source of Endogenous Bioactive Peptides: The Concept of Tissue-Specific Peptide Pool," Biopolymers, 1997, pp. 171-188, vol. 39.

Khavinson et al, Gerontological Aspects of Genome Peptide Regulation, 2005, S. Karger AG, Basel, Switzerland.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Effects of Short Peptides on Lymphocyte Chromatin in Senile Subjects," Bulletin of Experimental Biology and Medicine, Jan. 2004, pp. 78-81, vol. 137, No. 1.

Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.

Khavinson et al., "Inductive Activity of Retinal Peptides," Bulletin of Experimental Biology and Medicine, Nov. 2002, pp. 482-484, vol. 134, No. 5.

Khavinson et al., "Mechanisms Underlying Geroprotective Effects of Peptides," Bulletin of Experimental Biology and Medicine, Jan. 2002, pp. 1-5, vol. 133, No. 1.

Khavinson et al., "Peptide Promotes Overcoming of the Division Limit in Human Somatic Cell," Bulletin of Experimental Biology and Medicine, May 2004, pp. 503-506, vol. 137, No. 5.

Morozov et al., "Natural and Synthetic Thymic Peptides as Therapeutics for Immune Dysfunction," Int. J. Immunopharmac., 1997, pp. 501-505, vol. 19, No. 9/10.

Abraham, E., "Coagulation Abnormalities in Acute Lung Injury and Sepsis," Am. J. Respir. Cell Mol. Biol., 2000, pp. 401-404, vol. 22.

Adib-Conquy et al., "NF-kappaB Expression in Mononuclear Cells in Patients with Sepsis Resembles That Observed in Lipopolysaccharide Tolerance," Am. J. Respir. Crit. Care Med., 2000, pp. 1877-1883, vol. 162.

Arima et al., "IL-2-Induced Growth of CD8+ T Cell Prolymphocytic Leukemia Cells Mediated by NF-kappaB Induction and IL-2 Receptor alpha Expression," Leukemia Research, 1998, pp. 265-273, vol. 22, No. 3.

Baeuerle et al., "Function and Activation of NF-kappaB in the Immune System," Annu. Rev. Immunol., 1994, pp. 141-179, vol. 12.

Bethea et al., "Traumatic Spinal Cord Injury Induces Nuclear Factor-kappaB Activation," The Journal of Neuroscience, May 1, 1998, pp. 3251-3260, vol. 18, No. 9.

Bodfish et al., "Treating the Core Features of Autism: Are We There Yet?" Mental Retardation and Developmental Disabilities Research Reviews, 2004, pp. 318-326, vol. 10.

Brown et al., "Two Forms of NF-kappaB1 (p105/p50) in Murine Macrophages: Differential Regulation by Lipopolysaccharide, Interleukin-2, and Interferon-gamma," Journal of Interferon and Cytokine Research, 1997, pp. 295-306, vol. 17.

Epinat et al., "Diverse agents act at multiple levels to inhibit the Rel/NF-kappaB signal transduction pathway," Oncogene, 1999, pp. 6896-6909, vol. 18.

Faust et al., "Disseminated intravascular coagulation and purpura fulminans secondary to infection," Bailliere's Clinical Haematology, 2000, 179-197, vol. 13. No. 2.

Jimenez-Garza et al., "Early Effects of Modulating Nuclear factor-kappaB Activation on Traumatic Spinal Cord Injury in Rats," Ann. N.Y Acad. Sci., 2005, pp. 148-150, vol. 1053.

Kidd et al., "Autism, An Extreme Challenge to Integrative Medicine. Part II: Medical Management," Alternative Medicine Review, 2002, pp. 472-499, vol. 7, No. 6.

Kronfol et al., "Cytokines and the Brain: Implications for Clinical Psychiatry," Am. J. Psychiatry, May 2000, pp. 683-694, vol. 157, No. 5.

Li et al., "NF-kappaB Regulation in the Immune System," Nature Reviews/Immunology, Oct. 2002, pp. 725-734, vol. 2.

Malek-Ahmadi, P., "Role of Cytokines in Psychopathology: Therapeutic Implications," Drug News Prospects, Jun. 1998, pp. 271-276, vol. 11, No. 5.

McBean et al., "Rodent Models of Global Cerebral Ischemia: A Comparison of Two-Vessel Occlusion and Four-Vessel Occlusion," Gen. Pharmac., 1998, pp. 431-434, vol. 30, No. 4.

Neely et al., "Then and now: Studies using a burned mouse model reflect trends in burn research over the past 25 years," Burns, 1999, pp. 603-609, vol. 25.

Traystman, R., "Animal Models of Focal and Global Cerebral Ischemia," ILAR Journal, 2003, pp. 85-95, vol. 44, No. 2.

Weinberger et al., "Mechanisms Mediating the Biologic Activity of Synthetic Proline, Glycine, and Hydroxyproline Polypeptides in Human Neurophils," Mediators of Inflammation, 2005, pp. 31-38, vol. 1.

Yang et al., "Increased cortical nuclear factor kappaB (NF-kappaB) DNA binding activity after traumatic brain injury in rats," Neuroscience Letters, 1995, pp. 101-104, vol. 197.

Cui et al., Am. J. Physiol. Integr. Comp. Physiol., 2004, pp. R699-R709, vol. 286.

Dwinnell et al., Atlas of Diseases of the Kidney, Blackwell Sciences, 1999, pp. 12.1-12.12, Ch. 12.

Kalns et al., Biochem. Biophys. Res. Comm., 2002, pp. 506-509, vol. 297.

Kalns et al., Biochem. Biophys. Res. Comm., 2002, pp. 41-44, vol. 292.

Merck Index, 17th ed. 1999, pp. 1145-1146, 1841-1848, 2539, 2551.

Merriam-Webster Medical Dictionary, 1994, p. 82.

Moayeri et al., Journal of Clinical Investigation, Sep. 2003, pp. 670-682, vol. 112, No. 5.

Ngo et al., The protein folding problem and tertiary structure prediction, 1994, pp. 492-494.

Pellizzari et al., FEBS Letters, 1999, pp. 199-204, vol. 462.

Connelly et al., Biphasic Regulation of NF-kB Activity Underlies the Pro- and Anti-inflammatory Actions of Nitric Oxide, The Journal of Immunology, 2001, pp. 3873-3881, 166, The American Association of Immunologists, USA.

Friedlander, Tackling anthrax, Nature, Nov. 8, 2001, pp. 160-161, vol. 414.

Iskandar et al., "Effects of a urinary factor from women in early pregnancy on HIV-a, SIV and associated disease," Nature Medicine, pril 1998, vol. 4, No. 4, pp. 428-434.

Lang et al., "Induction of apoptosis in Kaposi's sarcoma spindle cell cultures by the subunits of human chorionic gonadtropin," AIDS 1997, vol. 11, No. 11, pp. 1333-1340.

Medzhitov, Toll-like Receptors and Innate Immunity, Nature Reviews/Immunology, Nov. 2001, pp. 135-145, vol. 1.

PCT International Search Report, PCT/NL01/00259, dated Dec. 18, 2001, 3 pages.

International Preliminary Examination Report, PCT/NI99/00313, dated Jul. 21, 2000, 6 pages.

PCT International Search Report, PCT/EP99/00313, dated Nov. 29, 1999, 3 pages.

Abeyama et al., A role of NF-κB-dependent gene transactivation in sunburn. The Journal of Clinical Investigation, vol. 105, No. 12, pp. 1751-1759, Jun. 2000.

Agawal et al., Acute Renal Failure, American Family Physician, 2000, pp. 2077-2088, vol. 61, corresponding to web version of p. 1-12.

Barton et al., Protective Role of Interleukin 6 in the Lipopolysaccharide-Galactosamine Septic Shock Model, Infection and Immunity, Apr. 1993, pp. 1496-1499, vol. 61, No. 4.

Baud et al., Signaling by proinflammatory cytokines: oligomerization of TRAF2 and TRAF6 is sufficient for JNK and IKK activation and target gene induction via an amino-terminal effector domain, Genes & Development, May 1999, pp. 1297-1308, vol. 13.

Borchardt, RT, Optimizing oral absorption of peptides using prodrug strategies, Journal of Controlled Release, Nov. 1999, pp. 231-238, vol. 62.

Bradham et al., Activation of nuclear factor-κB during orthotopic liver transplantation in rats is protective and does not require Kuppfer cells, Liver Transplantation and Surgery, Jul. 1999, pp. 282-293, vol. 5, No. 4.

Burdelya et al., NF-kappaB activating proteins as radioprotectants: Derivatives of Flagellin from Salmonella protect mice from hematopoietic and gastrointestinal Radiation Syndromes, Cleveland Biolabs, Inc, Division of Space Life Sciences Annual Meeting 2004.

Burdelya et al., An agonist of toll-like receptor 5 has radioprotective activity in mouse and primate models, Abstract, Science, Apr. 11, 2008, pp. 226-230, vol. 320, No. 5873.

Cleveland BioLabs, Inc., Radiation Antidote for Defense, (visited Apr. 16, 2008) <http://www.cbiolabs.com/Applications.php.

Cook et al., Modified total lymphoid irradiation and low dose coricosteroids in progressive multiple sclerosis, Journal of Neurological Sciences, vol. 152, pp. 172-181, 1997.

Corvino et al., Availability, stability and sterility of pralidoxime for mass casualty use, Abstract, Ann Emerg Med., Mar. 2006, pp. 272-277, vol. 47, No. 3.

Daemen et al., Ischemia-reperfusion-induced IFN-gamma up-regulation: involvement of IL-12 and IL-13, The Journal of Immunology, 1999, pp. 5506-5510, vol. 162.

De Saizieu et al., Journal of Bacteriology, vol. 182, No. 17, pp. 4696-4703, Sep. 2000.

Dechend et al., Oncogene, vol. 18, pp. 3316-3323, 1999.

Dietrich et al., Postischemic hypothermia and IL-10 treatment provide long-lasting neuroprotection fo CAI hippocampus following transient global ischemia in rats. Experimental Neurology, 1999, pp. 444-450, vol. 158.

Donnahoo et al., Early kidney TNF-alpha expression mediates neutrophil infiltration and injury after renal ischemia-reperfusion, American Journal of Physiology, Sep. 1999, pp. R922-R929, vol. 277, No. 3, Pt. 2.

Eckardt et al., Hypoxia-induced accumulation of erythropoietin mRNA in isolated hepatocytes is inhibited by protein kinase C, Pflugers Archiv., 1994, pp. 21-30, vol. 426.

Engles et al., Exogenous human recombinant interleukin-10 attenuates hindlimb ischemia-repferusion injury, Journal of Surgical Research, 1997, pp. 425-428, vol. 69.

Fassio et al., Transforming Growth Factor Alpha and Its Receptor in Neural Retina, Investigative Ophthalmology & Visual Science, Sep. 1989, pp. 1916-1922, vol. 30, No. 9.

GenBank Accession No. NP_000728, GI: 4502789, publicly available Apr. 2007.

Garkavtsev et al., Suppression of the novel growth inhibitor p33ING1 promotes neoplastic transformation, Nature Publishing Group, Dec. 14, 1996, pp. 415-420.

Garkavtsev et al., The candidate tumour suppressor p33ING1 cooperates with p53 in cell growth control, Nature, Jan. 15, 1998, pp. 295-298, vol. 391.

Gudkov, Andrei V., Cancer drug discovery: the wisdom of imprecision, Nature Medicine, Dec. 2004, 1298-00, vol. 10, No. 12.

Gudkov et al., The role of p53 in determining sensitivity to radiotherapy, Nature Reviews, Feb. 2003, pp. 117-129, vol. 3.

Gudkov, Andrei V., Converting p53 from a killer into a healer, Nature Medicine, Nov. 2002, pp. 1196-1198, vol. 8, No. 11.

Han et al., Cholecystokinin induction of mob-1 chemokine expression in pancreatic acinar cells requires NF-kappaB activation, American Journal of Physiology, Jul. 1999, vol. 277, pp. C74-C82.

Huang et al., Ischemia-reperfusion and immediate T cell responses, Cellular Immunology, 2007, pp. 4-11, vol. 248.

Husek et al., Rapid screening of urinary proline-hydroxyproline dipeptide in bone turnover studies, Abstract, J. Chromatogr B Analyt Technol Biomed Life Sci., Feb. 5, 2002, pp. 169-174, vol. 767, No. 1.

Ichiyama et al., Systemically administered alpha-melanocyte-stimulating peptides inhibit NF-kappaB activation in experimental brain inflammation, Brain Research, Jul. 1999, pp. 31-37, vol. 836.

Iyer et al., The transcriptional program in the response of human fibroblasts to serum, Science, Jan. 1999, pp. 83-87, vol. 283, No. 5398.

Keeton and Gould, Biological Science, 5th Ed., New York, W.W. Norton & Company, Inc. 1993, p. 4.

Lane et al., Interleukin-10 reduces the systemic inflammatory response in a murine model of intestinal ischemia/reperfusion, Surgery, 1997, pp. 288-294, vol. 122, No. 2.

Le Moine et al., Cold liver ischemia-reperfusion injury critically depends on liver T cells and is improved by donor pretreatment with interleukin 10 in mice, Hepatology, 2000, pp. 1266-1274, vol. 31, No. 6.

Lin et al., The Journal of Biological Chemistry, vol. 270, No. 24, pp. 14255-14258, Jun. 1995.

Lutterova et al., Marked difference in tumor necrosis factor-alpha expression in warm ischemia- and cold ischemia-reperfusion of the rat liver, Cryobiology, 2000, pp. 301-314, vol. 41.

Manna et al., Human chorionic gonadotropin suppresses activation of nuclear transcription factor-kappa B and activator protein-1 induced by tumor necrosis factor, The Journal of Biological Chemistry, May 2000, pp. 13307-13314, vol. 275, No. 18.

MedlinePlus, Medical Encyclopedia: autoimmune disorders (www.nlm.gov/medlineplus/ency/article/000816.htm), printed Jun. 7, 2007.

Ohlsson et al., Interleukin-1 Receptor Antagonist Reduces Mortality from Endotoxin Shock, Nature, Dec. 6, 1990, pp. 550-552, vol. 348.

Oka et al., Immunosuppression in organ transplantation, Japanese Journal of Pharmacology, vol. 71, No. 2, pp. 89-100, Jun. 1996.

Olszyna et al., Levels of Inhibitors of Tumor Necrosis Factor Alpha and Interleukin 1b in Urine and Sera of Patients with Urosepsis, Infection and Immunity, Aug. 1998, pp. 3527-3534.

Padmos et al., A discriminating messenger RNA signature for bipolar disorder formed by an aberrant expression of inflammatory genes in monocytes, Arch Gen Psychiatry, Apr. 2008, pp. 395-407, vol. 65, No. 4.

Pan et al., Bradykinin Stimulates NF-κB Activation and Interleukin 1β Gene Expression in Cultured Human Fibroblasts, J. Clin. Invest., Nov. 1996, pp. 2042-2049, vol. 93, No. 9, The American Society for Clinical Investigation, Inc.

Partial European Search Report for 02 763 111.8 dated Nov. 23, 2007.

PCT International Search Report and Written Opinion, PCT/NL2007/050092, dated Jul. 6, 2007.

PCT International Search Report, PCT/CA97/00568, dated Apr. 30, 1998.

Qin et al., Nuclear Factor kB Nuclear Translocation Upregulates c-Myc and p53 Expression during NMDA Receptor-Mediated Apoptosis in Rat Striatum, The Journal of Neuroscience, May 15, 1999, pp. 4023-4033, vol. 19, No. 10.

Quillan et al., Combinatorial diffusion assay used to identify topically active melanocyte-stimulating hormone receptor antagonists, PNAS, Mar. 1995, pp. 2894-2898, vol. 92, USA.

Redon et al., Global variation in copy number in the human genome, Nature, Nov. 23, 2006, pp. 444-454, vol. 444.

"RDT&E Budget item justification sheet" StartDateMarker 1999, EndDateMarker Retrieved from the Internet: URL:http://www.dtic.mil/descriptivesum/Y2000/OSD/PE0602787D.pdf>.

Riera et al., Neutrophils accentuate renal cold ischemia-reperfusion injury. Dose-dependent protective effect of platelet-activating factor receptor antagonist, The Journal of Pharmacology and Experimental Therapeutics, 1997, pp. 786-794, vol. 280, No. 2.

Rodriguez et al., Expression of human HLA-B27 transgene alters susceptibility to murine theiler's virus-induced demylenination, 1991, vol. 146, pp. 2596-2602.

Selzman et al., Interleukin-10 inhibits postinjury tumor necrosis factor-mediated human vascular smooth muscle proliferation, Journal of Surgical Research, 1998, pp. 352-356, vol. 80.

Sharma, Septic Shock, (visited Sep. 27, 2007 <http://www.emedicine.com/MED/topic2101.htm>.

Sovak et al., Aberrant nuclear factor-kappa B/Rel expression and the pathogenesis of breast cancer, The Journal of Clinical Investigation, Dec. 1997, pp. 2952-2960, vol. 100, No. 12.

Strom et al., Small-molecule inhibitor of p53 binding to mitochondria protects mice from gamma radiation, Nature Chemical Biology, Sep. 2006, pp. 474-479, vol. 2, No. 9.

Szinicz, L., History of chemical and biological warfare agents, Abstract, Toxicology, Oct. 30, 2005, pp. 167-181, vol. 214, No. 3.

Thibonnier et al., Cytoplasmic and nuclear signaling pathways of V1-vascular vasopressin receptors, Regulatory Peptides, 1993, pp. 79-84, vol. 45.

Valore et al., Human b-Defensin-1: An antimicrobial Peptide of Urogenital Tissues, J. Clin. Invest., Apr. 1998, pp. 1633-1642, vol. 101, No. 8.

Wallraff et al., Urinary Excretion of Amino Acids in Pregnancy, J. Clinc. Invest., 1950, pp. 1542-1544, vol. 29.

Wu et al., Gonadotropin-Releasing Hormone (GNRH) Cleavage Products are Involved in the Regulation of GNRH Gene Expression in the GT1-7 Neuronal Cell Line, Society for Neuroscience Abstracts, Nov. 4, 2000, pp. 7.8, XP009091566, vol. 26, No. 1-2.

Zhou et al., Transplantation tolerance in NF-κB-impaired mice is not due to regulation but is prevented by transgenic expression of Bcl-xL. The Journal of Immunology, vol. 174, No. 6, pp. 3447-3453, Mar. 2005.

* cited by examiner

TREATMENT OF MULTIPLE SCLEROSIS (MS)

CROSS-REFERENCE TO RELATED APPLICATION

This application is a continuation-in-part of the earlier U.S. patent application Ser. No. 10/028,075, filed Dec. 21, 2001, pending, the content of the entirety of which is incorporated by this reference.

TECHNICAL FIELD

The current invention relates to the body's innate way of modulation of important physiological processes and builds on insights reported in PCT International Publications WO99/59617 and WO01/72831 and PCT International patent application PCT/NL02/00639, the contents of all of which are incorporated by this reference.

BACKGROUND

In the aforementioned earlier patent applications, small gene-regulatory peptides are described that are present naturally in pregnant women and are derived from proteolytic breakdown of placental gonadotropins such as human chorionic gonadotropin (hCG) produced during pregnancy. These peptides (in their active state often only at about 4 to 6 amino acids long) were shown to have unsurpassed immunological activity that they exert by regulating expression of genes encoding inflammatory mediators such as cytokines. Surprisingly, it was found that breakdown of hCG provides a cascade of peptides that help maintain a pregnant woman's immunological homeostasis. These peptides are nature's own substances that balance the immune system to assure that the mother stays immunologically sound while her fetus does not get prematurely rejected during pregnancy as if it were a transplant but instead is safely carried through its time of birth.

Where it was generally thought that the smallest breakdown products of proteins have no specific biological function on their own (except to serve as antigen for the immune system), from the above three patent applications, it now emerges that the body in fact routinely utilizes the normal process of proteolytic breakdown of the proteins it produces to generate important gene-regulatory compounds, short peptides that control the expression of the body's own genes. Apparently the body uses a gene-control system ruled by small broken down products of the exact proteins that are encoded by its own genes.

It has been known that during pregnancy the maternal system introduces a status of temporary immuno-modulation which results in suppression of maternal rejection responses directed against the fetus. Paradoxically, during pregnancy, often the mother's resistance to infection is increased and she is found to be better protected against the clinical symptoms of various auto-immune diseases such as rheumatism and multiple sclerosis. The protection of the fetus can thus not be interpreted only as a result of immune suppression. Each of the above three applications have provided insights by which the immunological balance between protection of the mother and protection of the fetus can be understood.

It was shown that certain short breakdown products of hCG (i.e., short peptides which can easily be synthesized, if needed modified, and used as pharmaceutical composition) exert a major regulatory activity on pro- or anti-inflammatory cytokine cascades that are governed by a family of crucial transcription factors, the NFκB family which stands central in regulating the expression of genes that shape the body's immune response.

Most of the hCG produced during pregnancy is produced by cells of the placenta, the exact organ where cells and tissues of mother and child most intensely meet and where-immuno-modulation is most needed to fight off rejection. Being produced locally, the gene-regulatory peptides which are broken down from hCG in the placenta immediately balance the pro- or anti-inflammatory cytokine cascades found in the no-mans land between mother and child. Being produced by the typical placental cell, the trophoblast, the peptides traverse extracellular space; enter cells of the immune system and exert their immuno-modulatory activity by modulating NFκB-mediated expression of cytokine genes, thereby keeping the immunological responses in the placenta at bay.

BRIEF SUMMARY OF THE INVENTION

It is herein postulated that the beneficial effects seen on the occurrence and severity of auto-immune disease in the pregnant woman result from an overspill of the hCG-derived peptides into the body as a whole; however, these effects must not be overestimated, as it is easily understood that the further away from the placenta, the less immuno-modulatory activity aimed at preventing rejection of the fetus will be seen, if only because of a dilution of the placenta-produced peptides throughout the body as a whole. However, the immuno-modulatory and gene-regulatory activity of the peptides should by no means only be thought to occur during pregnancy and in the placenta; man and women alike produce hCG, for example in their pituitaries, and nature certainly utilizes the gene-regulatory activities of peptides in a larger whole.

Consequently, a novel therapeutic inroad is provided, using the pharmaceutical potential of gene-regulatory peptides and derivatives thereof. Indeed, evidence of specific up- or down-regulation of NFκB driven pro- or anti-inflammatory cytokine cascades that are each, and in concert, directing the body's immune response was found in silico in gene-arrays by expression profiling studies, in vitro after treatment of immune cells and in vivo in experimental animals treated with gene-regulatory peptides. Also, considering that NF-κB is a primary effector of disease (A. S. Baldwin, J. Clin. Invest., 2001, 107:3-6), using the hCG derived gene-regulatory peptides offer significant potential for the treatment of a variety of human and animal diseases, thereby tapping the pharmaceutical potential of the exact substances that help balance the mother's immune system such that her pregnancy is safely maintained.

DETAILED DESCRIPTION OF THE INVENTION

This invention in particular relates to the treatment of multiple sclerosis, and in particular to the treatment of the inflammatory injury seen in the progressive stages in the disease such as seen with the recurrent upsurges of acute disease, classically known as relapses or exacerbations, herein identified as relapsing/remitting disease seen with multiple sclerosis (MS).

Multiple sclerosis (MS) is the prototype inflammatory autoimmune disorder of the central nervous system and, with a lifetime risk of one in 400, potentially the most common cause of neurological disability in young adults. In experimental animals, an experimental autoimmune/allergic encephalomyelitis (EAE) can be induced in which MS is studied. Exacerbations in EAE and MS both are dramatically mediated by cytokines and chemokines. During an exacerbation, the TNF-α family and other pro-inflammatory cytokines is highly elevated in CSF. As with all complex traits, the disorder results from an interplay between as yet unidentified environmental factors and susceptibility genes. Together, these factors trigger a cascade of events, involving engagement of the immune system, acute inflammatory injury of axons and glia, recovery of function and structural repair, post-inflammatory gliosis, and neurodegeneration. The sequential involvement of these processes underlies the clinical course characterized by episodes with recovery, episodes leaving persistent deficits, and secondary progression. Despite limited success in each of these categories, everyone touched by multiple sclerosis looks for a better dividend from applying an improved understanding of the pathogenesis to clinical management.

Now, multiple sclerosis is recognized throughout the world, with around 2-5 million affected individuals. For the pathologist, multiple sclerosis is a disorder of the central nervous system (CNS), manifesting as acute focal inflammatory demyelination and axonal loss with limited remyelination, culminating in the chronic multifocal sclerotic plaques from which the disease gets its name. Demyelination in MS develops by a T-cell driven inflammatory process. Thus, the primary nature of inflammation is undisputed and will remain central for treatments that modulate the immune system. There are, however, several aspects that limit the therapeutic efficacy of strategies directed exclusively against the inflammatory component of the disease. Currently, immune suppression is unable to stop the inflammatory regimes using interferon β or co-polymer I, these treatments may decrease, but do not abolish, inflammation. Furthermore, it is currently not possible to intervene more specifically in the inflammatory process because neither the trigger of inflammation (virus-induced versus autoimmunity) nor the specific target antigen in the CNS of affected patients is known.

For the patient, multiple sclerosis entails an apparently infinite variety of symptoms but with certain recurring themes and an unpredictable course. For the neurologist, multiple sclerosis is a disorder of young adults diagnosed on the basis of clinical and paraclinical evidence for a least two demyelinating lesions, affecting different sites within the brain of spinal cord, separated in time. For the clinical scientist, multiple sclerosis is the prototype inflammatory autoimmune disease of the central nervous system in which knowledge gained across a range of basic and clinical neuroscience disciplines has already allowed rational strategies for treatment. For all these groups, multiple sclerosis remains a difficult disease for which solutions seem attainable yet remain elusive.

The oligodendrocyte, a principal target of immune attack in multiple sclerosis, synthesizes and maintains the myelin sheath of up to 40 neighboring nerve axons in the central nervous system. Compact myelin consists of a condensed membrane, spiraled around axons to form the insulating segmented sheath needed for a saltatory axonal conduction: voltage-gated sodium channels cluster at the unmyelinated nodes of Ranvier, between myelin segments, from where the action potential is propagated and spreads passively down the myelinated nerve segment to trigger another action potential at the next node. The consequences of demyelination for saltatory conduction explain many clinical and laboratory features of multiple sclerosis. Partially demyelinated axons conduct impulses at reduced velocity—explaining the characteristic delays in conduction of evoked potentials. Demyelinated axons can discharge spontaneously and show increased mechanical sensitivity—accounting for the flashes of light on eye movement (phosphenes) and electrical sensation running down the spine or limbs on neck flexion (Lhermitte's symptom and sign). Partially demyelinated axons, whose safety factor for conduction is compromised, cannot sustain the fall in membrane capacitance induced by a rise in temperature, and conduction fails—leading to the characteristic appearance of symptoms and signs after exercise or a hot bath (Uhthoff's phenomenon). Ephaptic transmission (cross-talk) can arise between neighboring demyelinated axons, resulting in paroxysmal symptoms—trigeminal neuralgia, ataxia, and dysarthria, or painful tetanic posturing of the limbs, lasting one or two minutes and often triggered by touch or movement. Individuals with multiple sclerosis characteristically tire during physical and cognitive tasks, and take longer to recover: although poorly understood, and probably multifactorial, fatigue in multiple sclerosis can be very disabling, even in isolation.

Multiple sclerosis affects twice as many women as it does men; this unexplained bias is similar to that seen in many other putative autoimmune diseases. The disease has an incidence of about seven per 100,000 every year, prevalence of around 120 per 100,000, and lifetime risk of one in 400. 80% of patients present with relapsing/remitting disease and, typically, the illness passes through phases of relapse with full recovery, relapse with persistent deficit, and secondary progression. In about a quarter of patients, multiple sclerosis never affects activities of daily living; conversely, up to 15% become severely disabled within a short time. Episodes happen at random intervals, but initially average about one per year, decreasing steadily thereafter. In 20% of patients, the disease is progressive from onset, hence termed primary progressive—affecting the spinal cord and, less frequently, the optic nerve, cerebrum, or cerebellum. Disease onset is usually in the third or fourth decade, but 2% of patients with multiple sclerosis present before age 10 years, and 5% before age 16 years. In children, the distinction from acute disseminated encephalomyelitis (ADEM) can often only be established by observing the subsequent natural history. Overall, life expectancy is at least 25 years from disease onset with most patients dying from unrelated causes.

Healthy individuals harbor autoreactive myelin T cells, presumed to normally be kept in check by regulatory T cells. One hypothesis to explain the breakdown of immune regulation in these autoimmune diseases is molecular mimicry, which suggests that peptide (the environmental factor), presented in the groove of specific HLA/MHC class II molecules (one component of inherited risk), is immunologically indistinguishable from self-antigen and, hence, an appropriate response to infection generates inappropriate inflammation against some component of the oligodendrocyte-myelin unit. In common with all organ-specific autoimmune diseases, this systemic defect results not in a sustained autoimmune attack on the entire target organ, but, rather, in inflammatory lesions that are temporally and spatially segregated.

Failure of regulation leads to proliferation, activation, and entry into the circulation of autoreactive T cells; they express adhesion molecules and induce reciprocal changes in endothelia, allowing access across the blood-brain barrier into the central nervous system. There, activated T cells re-encounter antigen and activate microglia (the CNS macrophage); these, in turn, express class II molecules, re-present antigen to T cells, and set up a proinflammatory loop, which provides an infiltrate rich in activated T cells and microglia with some neutrophils.

Toxic inflammatory mediators are released, sustaining breakdown of the blood-brain barrier and leading to injury of axons and glia. Nitric oxide might act directly on normal or hypomyelinated axons, transiently blocking conduction and reversibly increasing deficits arising from already compromised pathways. As acute inflammation resolves, pathways are released from nitric oxide-induced physiological conduction block. Symptoms also improve as surviving functional pathways are reorganized at the cellular and systems level. Together, these mechanisms account for remission early in the disease. But tissue vulnerability is easily exposed. When compounded by high axonal firing frequency, nitric oxide causes structural (and hence irreversible) changes to axons. Axonal transection in acute inflammatory plaques is shown histologically and radiologically through reduction in the neuronal spectroscopic marker, N-acetyl aspartate (NAA). These transected axons undergo Wallerian degeneration during the subsequent 18 months, but this action does not seem to extend the lesion or shape the clinical deficit.

Cytokines and growth-promoting factors released by reactive astrocytes and microglia as part of the acute inflammatory process promote endogenous remyelination. But, over time, astrocyte reactivity seals the lesion and gliosis causes a physical barrier to further remyelination, reducing the capacity to accommodate cumulative deficits, and marking transition to the stage of persistent deficit.

Since permanent disability can be caused by incomplete recovery from disease episodes, relapse frequency is bound to correlate with accumulation of disability during the relapsing-remitting phase of multiple sclerosis. Type-1 interferons were first used in multiple sclerosis for their anti-viral action, in view of the propensity of viral infections to trigger relapses. In fact, their mechanism of action is immunological and complex: we prefer the evidence for functional antagonism of proinflammatory cytokines and downregulation of class II MHC antigen expression; but other modes of action—including effects on the blood brain barrier (BBB)—can equally well be argued.

Only in trials of the two interferon β-1a preparations, not interferon β-1b, was this change in relapse rate also accompanied by reduction in the accumulation of disability. But this reduction could be accounted for by a fall in the accumulation of relapse-related deficits, rather than an effect on secondary progression.

Three other agents reduce relapse frequency, and the accumulation of disability, in relapsing-remitting multiple sclerosis; each has similar efficacy to the β-interferons and acceptable adverse effects profiles. Glatiramer acetate (Copaxone, Teva), a mixture of synthetic polypeptides was noted serendipitously to suppress experimental autoimmune/allergic encephalomyelitis, perhaps by inhibiting the binding of myelin basic protein (MBP) to the T-cell receptor or by altering the phenotype of myelin-autoreactive T cells. The drug is licensed for the treatment of relapsing-remitting multiple sclerosis in the USA and in Europe on the basis of results from a trial of 251 patients, in which the annual relapse rate was reduced by 25% in the treated group.

Azathioprine inhibits lymphocyte proliferation by inhibiting purine synthesis, and probably has similar efficacy to the β interferons, although the trial data were obtained in a less rigorous manner and reported more candidly.

Mitoxantrone inhibits DNA repair and synthesis in dividing and non-dividing cells through inhibition of DNA topoisomerase II; it is potentially much more toxic than the β interferons, but has a USA license for the treatment of aggressive relapsing disease, including patients with high relapse frequency in the progressive phase.

In view of the fact that the ability to suppress relapses and limit their consequences is partial, no informed analyst could reasonably conclude that (despite their achievements) the β-interferons are a definitive therapy in multiple sclerosis. The pharmaceutical industry has responded by sponsoring studies with combinations of established drugs (such as β interferon and cyclophosphamide) without compelling evidence for synergistic benefit to date, together with a significant investment in novel immunotherapeutic strategies. Interferon β-1b and β-1a and glatiramer acetate are widely prescribed in North America to patients with relapsing MS. However, these drugs have significant limitations, including cost (US $ 11.000 per year), inconvenience (parenteral administration), frequency of adverse effects (especially "flu-like" symptoms for several hours in many patients after each injection of interferon) and a relatively modest overall impact on disease course (for example, reductions in relapse rate of less than 35%). Furthermore the therapeutic effect of interferon β more than 1 year after onset of treatment in relapsing-remitting MS is unclear. The National Multiple Sclerosis Society has issued a practice directive recommending the use of these medications by all patients with clinically significant, relapsing MS. Other therapies directed against MS include the treatment of the MS patient with a (monoclonal) antibody directed against a cytokine, such as TNF-α, IL-6 or IL-12, However, although few would disagree that using these cytokine-blocking agents such as anti-TNF-α therapy may be an important therapeutic addition in the treatment of patients with MS, adverse effects related to single cytokine neutralizing therapies have emerged. Also, for unknown reasons, single cytokine blocking proteins may cause the formation of anti-dsDNA antibodies, and after repeated treatment the cumulative ANA incidence can be as high as 50%. Nonetheless, anti-TNF-α antibody therapy is associated with lupus-like symptoms. Also, demyelinizing disease and aplastic anemia have been reported in a small number of thus treated patients. A major problem of repeated administration of chimeric therapeutic antibodies is immunogenicity, and up to 60% of antibody treated patients develop human antichimeric antibodies (HACAs) which are related to infusion reactions and reduce therapeutic efficacy.

The invention provides a method for the treatment of a, in particular human, subject believed to be suffering of multiple sclerosis, with a specific aim to reduce the frequency, and limit the lasting effects, of relapses or exacerbations, to relieve symptoms that arise from the release of additional pro-inflammatory cytokines during the relapse, to prevent disability arising from disease progression, and promote tissue repair. The invention provides a pharmaceutical composition for the treatment of relapsing/remitting multiple sclerosis occurring in a subject, in particular in a human, and a method for the treatment of the exacerbations associated with additional pro-inflammatory cytokine release, for example in a primate suffering from MS or EAE comprising subjecting the subject to a signaling molecule according to the invention, preferably to a mixture of such signaling molecules.

Furthermore, the invention provides a method for the prevention of the development of multiple sclerosis in a subject believed to be in need thereof, in particular for the treatment of a human being after a sign of neurological failure, such as neuritis optica has been observed but MS has not developed, and use of a signaling molecule according to the invention for the production of a pharmaceutical composition for the prevention of multiple sclerosis, for treatment of relapsing/remitting multiple sclerosis occurring in a subject, in particular in a human being, and a method for the treatment of the exacerbations associated with additional pro-inflammatory cytokine release, in particular in a human being.

Administration of such a signaling molecule or mixture preferably occurs systemically, e.g., by intravenous, intramuscular, intraperitoneal or subcutaneous administration and leads to a dampening of the effect of the additionally released pro-inflammatory cytokines during the exacerbation phase. In severe cases, intrathecal administration may be considered.

The invention is further explained with the aid of the following illustrative examples.

EXAMPLES

In a preferred embodiment, the invention provides a method for modulating relapsing/remitting disease of MS in a subject believed to be in need thereof comprising providing the subject with a signaling molecule comprising a short, gene regulatory peptide or functional analogue thereof, wherein the signaling molecule is administered in an amount sufficient to modulate the iatrogenic event. The signal molecule is preferably a short peptide, preferably of at most 30 amino acids long, or a functional analogue or derivative thereof. In a much preferred embodiment, the peptide is an oligopeptide of from about 3 to about 15 amino acids long, preferably 4 to 12, more preferably 4 to 9, most preferably 4 to 6 amino acids long, or a functional analogue or derivative thereof. Of course, such a signaling molecule can be longer, for example by extending it (N- and/or C-terminally), with more amino acids or other side groups, which can for example be (enzymatically) cleaved off when the molecule enters the place of final destination. In particular a method is provided wherein the signaling molecule modulates translocation and/or activity of a gene transcription factor. It is particularly useful when the gene transcription factor comprises an NF-κB/Rel protein or an AP-1 protein. Many of the relapsing/remitting events as mentioned above induce increased expression of inflammatory cytokines due to activation of NF-κB and AP-1, and in a preferred embodiment the invention provides a method wherein translocation and/or activity of the NF-κB/Rel protein or AP-1 protein is inhibited. In one embodiment, the peptide is selected from the group of peptides LQG, AQG, LQGV (SEQ ID NO: 1), AQGV (SEQ ID NO: 2), LQGA (SEQ ID NO: 3), VLPALP (SEQ ID NO: 4), ALPALP (SEQ ID NO: 5), VAPALP (SEQ ID NO: 6), ALPALPQ (SEQ ID NO: 7), VLPAAPQ (SEQ ID NO: 8), VLPALAQ (SEQ ID NO: 9), LAGV (SEQ ID NO: 10), VLAALP (SEQ ID NO: 11), VLPALA (SEQ ID NO: 12), VLPALPQ (SEQ ID NO: 13), VLAALPQ (SEQ ID NO: 14), VLPALPA (SEQ ID NO: 15), GVLPALP (SEQ ID NO: 16), LQGVLPALPQVVC (SEQ ID NO: 17), LPGCPRGVNPVVS (SEQ ID NO: 18), LPGC (SEQ ID NO: 19), MTRV (SEQ ID NO: 20), MTR, VVC. As the, additional expression of inflammatory cytokines is often due to activation of NF-κB and AP-1. Inflammatory cytokines can be expressed by endothelium (for example, by trauma), perivascular cells and adherent or transmigrating leukocytes, inducing numerous pro-inflammatory and procoagulant effects. Together these effects predispose to inflammation, thrombosis and hemorrhage. Of clinical and medical interest and value, the present invention provides the opportunity to selectively control NFκB-dependent gene expression in tissues and organs in a living subject, preferably in a primate, allowing upregulating essentially anti-inflammatory responses such as IL-10, and downregulating essentially pro-inflammatory responses such as mediated by TNF-α, nitric oxide (NO), IL-5, IL-6, IL-12 and IL-1β.

In comparison with single cytokine therapy, such as the use of anti-TNF-α, anti IL-5, anti-IL-6, anti-IL-12, anti-IL-23, anti-IL-12p40, anti-IL23p40 or anti-IL-1β: antibodies, using an NFκB down-regulating peptide or functional analogue thereof according to the invention has the major advantage that a major network of pro-inflammatory cytokines is down-regulated.

The invention thus provides use of an NFκB regulating peptide or derivative thereof for the production of a pharmaceutical composition for the treatment of relapsing/remitting disease seen with MS, preferably in a primate, and provides a method of treatment of relapsing/remitting disease seen with MS, notably in a primate. It is preferred that the treatment comprises administering to the subject a pharmaceutical composition comprising an NFκB down-regulating peptide or functional analogue thereof. Examples of useful NFκB down-regulating peptides are VLPALPQVVC (SEQ ID NO: 21), LQGVLPALPQ (SEQ ID NO: 22), LQG, LQGV (SEQ ID NO: 1), GVLPALPQ (SEQ ID NO: 23), VLPALP (SEQ ID NO: 4), VVC, MTR and circular LQGVLPALPQVVC (SEQ ID NO: 17). More down-regulating peptides and functional analogues can be found using the methods as provided herein. Most prominent among NFκB down-regulating peptides are VLPALPQVVC (SEQ ID NO: 21), LQGVLPALPQ (SEQ ID NO: 22), LQG, LQGV (SEQ ID NO: 1), and VLPALP (SEQ ID NO: 4). These are also capable of reducing production of NO by a cell.

In one embodiment, the invention provides a method of treating a subject suffering from a relapsing/remitting disease seen with MS with a method and signaling molecule according to the invention concomitantly, or at least timely, with a treatment with a single cytokine blocking protein, such as an anti-TNF-α, anti IL-5, anti-IL-6, anti-IL-12, anti-IL-23, anti-IL-12p40, anti-IL23p40or anti-IL-1β antibody or functional analogue thereof. It is herein also provided to use a signaling molecule according to the invention for the production of a pharmaceutical composition for the treatment of a subject believed to be suffering of MS and receiving treatment with an anti-TNF-α, anti IL-5, anti-IL-6, anti-IL-12, anti-IL-23, anti-IL-12p40, anti-IL23p40or anti-IL-1βantibody. It is herein also provided to use a composition that comprises at least two oligopeptides or functional analogues thereof, each capable of down-regulation NFκB, and thereby reducing production of NO and/or TNF-α by a cell, in particular wherein at least two oligopeptides are selected from the group LQGV (SEQ ID NO: 1), AQGV (SEQ ID NO: 2) and VLPALP (SEQ ID NO: 4), for the treatment of relapsing/remitting disease seen with MS. In response to a variety of signals received by the body in the course of the relapsing-remitting disease seen with MS, the NFκB/Rel family of transcription factors is activated and form different types of hetero- and homodimers among themselves to regulate the expression of target genes containing κB-specific binding sites. NF-κB transcription factors are hetero- or homodimers of a family of related proteins characterized by the Rel homology domain. They form two subfamilies, those containing activation domains (p65-RELA, RELB, and c-REL) and those lacking activation domains (p50, p52). The prototypical NFκB is a heterodimer of p65 (RELA) and p50 (NF-κB1). Among the activated NFκB dimers, p50-p65 heterodimers are known to be involved in enhancing the transcription of target genes and p50-p50 homodimers in transcriptional repression. However, p65-p65 homodimers are known for both transcriptional activation and repressive activity against target genes. κB DNA binding sites with varied affinities to different NFB dimers have been discovered in the promoters of several eukaryotic genes and the balance between activated NFκB homo- and heterodimers ultimately determines the nature and level of gene expression within the cell. The term "NFκB-regulating peptide" as used herein refers to a peptide or a modification or derivative thereof capable of modulating the activation of members of the NFκB/Rel family of transcription factors. Activation of NFκB can lead to enhanced transcription of target genes. Also, it can lead to transcriptional repression of target genes. NFκB activation can be regulated at multiple levels. For example, the dynamic shuttling of the inactive NFκB dimers between the cytoplasm and nucleus by IκB proteins and its termination by phosphorylation and proteasomal degradation, direct phosphorylation, acetylation of NFκB factors, and dynamic reorganization of NFκB subunits among the activated NFκB dimers have all been identified as key regulatory steps in NFκB activation and, consequently, in NFκB-mediated transcription processes. Thus, an NFκB-regulating peptide is capable of modulating the transcription of pro-inflammatory cytokine genes that are under the control of NFκB/Rel family of transcription factors. Modulating comprises the upregulation or the downregulation of transcription. In a preferred embodiment, a peptide according to the invention, or a functional derivative or analogue thereof is used for the production of a pharmaceutical composition for the treatment of relapsing/remitting disease seen with MS. NFκB regulating peptide can be given concomitantly to other MS treatments, the peptide (or analogue) concentration preferably being from about 1 to about 1000 mg/l, but the peptide can also been given on its own, for example in a bolus injection. Doses of 1 to 5 mg/kg bodyweight, for example every eight hours in a bolus injection or per infusionem until the patient stabilizes, are recommended. For example in cases where large adverse response are expected or diagnosed, it is preferred to monitor cytokine profiles, such as TNF-α, IL-6 or IL-10 levels, in the plasma of the treated patient, and to stop treatment according to the invention when these levels are normal. In a preferred embodiment it is herein provided to give a patient experiencing a severe and acute exacerbation with a bolus injection of NF-κB down-regulating peptide such as AQGV (SEQ ID NO: 2), LQGV (SEQ ID NO: 1) or VLPALP (SEQ ID NO: 4) at 2 mg/kg and continue the infusion with an NF-κB down regulating peptide such as AQGV (SEQ ID NO: 2), LQGV (SEQ ID NO: 1) or VLPALP (SEQ ID NO: 4) or a functional analogue thereof at a dose of 1 mg/kg bodyweight for every eight hours. Dosages may be increased or decreased, for example depending on the outcome of monitoring the cytokine profile in the plasma or CSF of the patient. As the, exacerbations and disease progression in experimental autoimmune/allergic encephalomyelitis (EAE) and MS both are dramatically mediated by cytokines and chemokines. During an exacerbation of MS, the TNF-α family is highly elevated in CSF and plasma. IL-12 activity is often also high. The downregulation or T cell regulation of these cytokines and chemokines can prevent T cell and dendritic cells from reaching the CNS and then further down regulate the proinflammatory response which produces demyelination of the brain and spinal cord. This model of migration of cells to the CNS and then the release of proinflammatory cytokines and chemokines is seen particularly in the course of relapsing/remitting disease and can be treated by a peptide according to the invention through NFκB regulation, the development of T regulator cells, and the intervention of expression of early or pregenes such as C-jun or C-erg. The treatment protocols as given herein can also be used for other diseases that resemble or include exacerbations of multiple sclerosis and its variants, additional pro-inflammatory cytokine release in EAE and other infectious and/or immune based meningoencephalopathies, such as seen with measles i.e. SSPE, mumps, infections with hemorrhagic viruses, Progressive Multifocal Encephalopathy or a papilloma virus (JC virus) disease, Bacterial Endocarditis inducing immune encephalopathy, malaria with cerebral encephalopathy, angiostrongyliasis and other parasitic encephalitis, Lyme Disease, Herpes 1-8 disease including the mono like viruses such as EBV, CMV, and HHV6, rickettsial disease, i.e., Typhus, Rocky Mountain Spotted Fever, and Q fever, Chlamydia disease, i.e., Trachoma, NSU, Chlamydial Pneumonia, mycoplasma arthritis and encephalitis, HIV-1 and 2 encephalitis and dementia, Arbovirus disease, Togavirus disease and other lentivirus or Bunya virus or Flavivirus disease. Other forms of infectious and/or inflammatory meningoecephalomyelites are acute bacterial infections, sprirochetal infections (neurolues, Lyme neuroborreliosis, tuberculosis, viral infections (enteroviruses, mumps, herpes simplex type 2, toga viruses (arbovirus), HIV type 1 and 2, HTLV-1 infections), fungal infections (*Cryptococcus neoformans*, *Coccidiodes immitis*, *Blastomyces dermatitidis*, *Paracoccidioides brasiliensis*, *sporothrix schenkii*, *Histoplasma capsulatum*, *Psuedallescheria boydii* and the dermatiaceous fungi, mostly opportunistic infections such as *candida* and *aspergillus* species and *zygomycetes*), protozoan infections (cerebral malaria, toxoplasmosis, trypanosoma species, naegleria species and helminths), neurosarcoidosis, Creutzfeldt-Jacob disease, and neurological complications following vaccination.

In response to a variety of pathophysiological and developmental signals, the NFκB/Rel family of transcription factors is activated and form different types of hetero- and homodimers among themselves to regulate the expression of target genes containing κB-specific binding sites. NF-κB transcription factors are hetero- or homodimers of a family of related proteins characterized by the Rel homology domain. They form two subfamilies, those containing activation domains (p65-RELA, RELB, and c-REL) and those lacking activation domains (p50, p52). The prototypical NFκB is a heterodimer of p65 (RELA) and p50 (NF-κB1). Among the activated NFκB dimers, p50-p65 heterodimers are known to be involved in enhancing the transcription of target genes and p50-p50 homodimers in transcriptional repression. However, p65-p65 homodimers are known for both transcriptional activation and repressive activity against target genes. κB DNA binding sites with varied affinities to different NFκB dimers have been discovered in the promoters of several eukaryotic genes and the balance between activated NFκB homo- and heterodimers ultimately determines the nature and level of gene expression within the cell. The term "NFκB-regulating peptide" as used herein refers to a peptide or a modification or derivative thereof capable of modulating the activation of members of the NFκB/Rel family of transcription factors. Activation of NFκB can lead to enhanced transcription of target genes. Also, it can lead to transcriptional repression of target genes. NFκB activation can be regulated at multiple levels. For example, the dynamic shuttling of the inactive NFκB dimers between the cytoplasm and nucleus by IκB proteins and its termination by phosphorylation and proteasomal degradation, direct phosphorylation, acetylation of NFκB factors, and dynamic reorganization of NFκB subunits among the activated NFκB dimers have all been identified as key regulatory steps in NFκB activation and, consequently, in NFκB-mediated transcription processes. Thus, an NFκB-regulating peptide is capable of modulating the transcription of genes that are under the control of the NFκB/Rel family of transcription factors. Modulation comprises the upregulation or the downregulation of transcription. In a preferred embodiment, a peptide according to the invention, or a functional derivative or analogue thereof is used for the production of a pharmaceutical composition. Examples of useful NFκB down-regulating peptides to be included in such a pharmaceutical composition are VLPALPQVVC (SEQ ID NO: 21), LQGVLPALPQ (SEQ ID NO: 22), LQG, LQGV (SEQ ID NO: 1), GVLPALPQ (SEQ ID NO: 23), VLPALP (SEQ ID NO: 4), VVC, MTR and circular LQGVLPALPQVVC (SEQ ID NO: 17). More gene-regulating peptides and functional analogues can be found in a (bio)assay, such as an NFκB translocation assay as provided herein. Most prominent among NFκB down-regulating peptides are VLPALPQVVC (SEQ ID NO: 21), LQGVLPALPQ (SEQ ID NO: 22), LQG, LQGV (SEQ ID NO: 1), and VLPALP (SEQ ID NO: 4). These are also capable of reducing production of NO by a cell. Furthermore, LQG, VVC and MTRV (SEQ ID NO: 20), and in particular LQGV (SEQ ID NO: 1) promote angiogenesis, especially in topical applications.

It is herein also provided to use a composition that comprises at least two oligopeptides or functional analogues thereof, each capable of down-regulation NFκB, and thereby reducing production of NO and/or TNF-α by a cell, in particular wherein the at least two oligopeptides are selected from the group LQGV (SEQ ID NO: 1), AQGV (SEQ ID NO: 2) and VLPALP (SEQ ID NO: 4). Useful NFκB up-regulating peptides are VLPALPQ (SEQ ID NO: 13), GVLPALP (SEQ ID NO: 16) and MTRV (SEQ ID NO: 20). As indicated, more gene-regulatory peptides may be found with an appropriate (bio)assay. A gene-regulatory peptide as used herein is preferably short. Preferably, such a peptide is 3 to 15 amino acids long, more preferably, wherein the lead peptide is 3 to 9 amino acids long, most preferred wherein the lead peptide is 4 to 6 amino acids long, and capable of modulating the expression of a gene, such as a cytokine, in a cell. In a preferred embodiment, a peptide is a signaling molecule that is capable of traversing the plasma membrane of a cell or, in other words, a peptide that is membrane-permeable.

Functional derivative or analogue herein relates to the signaling molecular effect or activity as for example can be measured by measuring nuclear translocation of a relevant transcription factor, such as NF-κB in an NF-κB assay, or AP-1 in an AP-1 assay, or by another method as provided herein. Fragments can be somewhat (i.e. 1 or 2 amino acids) smaller or larger on one or both sides, while still providing functional activity. Such a bioassay comprises an assay for obtaining information about the capacity or tendency of a peptide, or a modification thereof, to regulate expression of a gene. A scan with for example a 15-mer, or a 12-mer, or a 9-mer, or a 8-mer, or a 7-mer, or a 6-mer, or a 5-mer, or a 4-mer or a 3-mer peptides can yield valuable information on the linear stretch of amino acids that form an interaction site and allows identification of gene-regulatory peptides that have the capacity or tendency to regulate gene expression. Gene-regulatory peptides can be modified to modulate their capacity or tendency to regulate gene expression, which can be easily assayed in an in vitro bioassay such as a reporter assay. For example, a particular amino acid at an individual position can be replaced with another amino acid of similar or different properties. Alanine (Ala)-replacement scanning, involving a systematic replacement of each amino acid by an Ala residue, is a suitable approach to modify the amino acid composition of a gene-regulatory peptide when in a search for a signaling molecule capable of modulating gene expression. Of course, such replacement scanning or mapping can be undertaken with amino acids other than Ala as well, for example with D-amino acids. In one embodiment, a peptide derived from a naturally occurring polypeptide is identified as being capable of modulating gene expression of a gene in a cell. Subsequently, various synthetic Ala-mutants of this gene-regulatory peptide are produced. These Ala-mutants are screened for their enhanced or improved capacity to regulate expression of a gene compared to gene-regulatory polypeptide.

Furthermore, a gene-regulatory peptide, or a modification or analogue thereof, can be chemically synthesized using D- and/or L-stereoisomers. For example, a gene-regulatory peptide that is a retro-inverso of an oligopeptide of natural origin is produced. The concept of polypeptide retro-inversion (assembly of a natural L-amino acid-containing parent sequence in reverse order using D-amino acids) has been applied successfully to synthetic peptides. Retro-inverso modification of peptide bonds has evolved into a widely used peptidomimetic approach for the design of novel bioactive molecules which has been applied to many families of biologically active peptides. The sequence, amino acid composition and length of a peptide will influence whether correct assembly and purification are feasible. These factors also determine the solubility of the final product. The purity of a crude peptide typically decreases as the length increases. The yield of peptide for sequences less than 15 residues is usually satisfactory, and such peptides can typically be made without difficulty. The overall amino acid composition of a peptide is an important design variable. A peptide's solubility is strongly influenced by composition. Peptides with a high content of hydrophobic residues, such as Leu, Val, Ile, Met, Phe and Trp, will either have limited solubility in aqueous solution or be completely insoluble. Under these conditions, it can be difficult to use the peptide in experiments, and it may be difficult to purify the peptide if necessary. To achieve a good solubility, it is advisable to keep the hydrophobic amino acid content below 50% and to make sure that there is at least one charged residue for every five amino acids. At physiological pH Asp, Glu, Lys, and Arg all have charged side chains. A single conservative replacement, such as replacing Ala with Gly, or adding a set of polar residues to the N- or C-terminus, may also improve solubility. Peptides containing multiple Cys, Met, or Trp residues can also be difficult to obtain in high purity partly because these residues are susceptible to oxidation and/or side reactions. If possible, one should choose sequences to minimize these residues. Alternatively, conservative replacements can be made for some residues. For instance, Norleucine can be used as a replacement for Met, and Ser is sometimes used as a less reactive replacement for Cys. If a number of sequential or overlapping peptides from a protein sequence are to be made, making a change in the starting point of each peptide may create a better balance between hydrophilic and hydrophobic residues. A change in the number of Cys, Met, and Trp residues contained in individual peptides may produce a similar effect. In another embodiment of the invention, a gene-regulatory peptide capable of modulating gene expression is a chemically modified peptide. A peptide modification includes phosphorylation (e.g., on a Tyr, Ser or Thr residue), N-terminal acetylation, C-terminal amidation, C-terminal hydrazide, C-terminal methyl ester, fatty acid attachment, sulfonation (tyrosine), N-terminal dansylation, N-terminal succinylation, tripalmitoyl-S-Glyceryl Cysteine (PAM3 Cys-OH) as well as farnesylation of a Cys residue. Systematic chemical modification of a gene-regulatory peptide can for example be performed in the process of gene-regulatory peptide optimization.

Synthetic peptides can be obtained using various procedures known in the art. These include solid phase peptide synthesis (SPPS) and solution phase organic synthesis (SPOS) technologies. SPPS is a quick and easy approach to synthesize peptides and small proteins. The C-terminal amino acid is typically attached to a cross-linked polystyrene resin via an acid labile bond with a linker molecule. This resin is insoluble in the solvents used for synthesis, making it relatively simple and fast to wash away excess reagents and by-products.

The peptides as mentioned in this document such as LQG, AQG, LQGV (SEQ ID NO: 1), AQGV (SEQ ID NO: 2), LQGA (SEQ ID NO: 3), VLPALP (SEQ ID NO: 4), ALPALP (SEQ ID NO: 5), VAPALP (SEQ ID NO: 6), ALPALPQ (SEQ ID NO: 7), VLPAAPQ (SEQ ID NO: 8), VLPALAQ (SEQ ID NO: 9), LAGV (SEQ ID NO: 10), VLAALP (SEQ ID NO: 11), VLPALA (SEQ ID NO: 12), VLPALPQ (SEQ ID NO: 13), VLAALPQ (SEQ ID NO: 14), VLPALPA (SEQ ID NO: 15), GVLPALP (SEQ ID NO: 16), VVCNYRDVRFE-SIRLPGCPRGVNPVVSYAVALSCQCAL (SEQ ID NO: 24), RPRCRPINATLAVEKEGCPVCITVNTTICAGYCPT (SEQ ID NO: 25), SKAPPPSLPSPSRLPGPS (SEQ ID NO: 26), LQGVLPALPQVVC (SEQ ID NO: 17), SIRLPGCPRGVNPVVS (SEQ ID NO: 27), LPGCPRGVN-PVVS (SEQ ID NO: 18), LPGC (SEQ ID NO: 19), MTRV (SEQ ID NO: 20), MTR, and VVC were prepared by solid-phase synthesis using the fluorenylmethoxycarbonyl (Fmoc)/tert-butyl-based methodology with 2-chlorotrityl chloride resin as the solid support. The side-chain of glutamine was protected with a trityl function. The peptides were synthesized manually. Each coupling consisted of the following steps: (i) removal of the α-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP) and (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/H$_2$O/triisopropylsilane (TIS) 95:2.5:2.5. After 30 minutes TIS was added until decolorization. The solution was evaporated in vacuo and the peptide precipitated with diethyl ether. The crude peptides were dissolved in water (50-100 mg/ml) and purified by reverse-phase high-performance liquid chromatography (RP-HPLC). HPLC conditions were: column: Vydac TP21810C18 (10×250 mm); elution system: gradient system of 0.1% TFA in water v/v (A) and 0.1% TFA in acetonitrile (ACN) v/v (B); flow rate 6 ml/min; absorbance was detected from 190-370 nm. There were different gradient systems used. For example for peptides LQG and LQGV (SEQ ID NO: 1): 10 minutes 100% A followed by linear gradient 0-10% B in 50 minutes. For example for peptides VLPALP (SEQ ID NO: 4) and VLPALPQ (SEQ ID NO: 13): 5 minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The elute was concentrated and lyophilized in 28 hours. Peptides later were prepared for use by dissolving them in PBS.

RAW 264.7 macrophages, obtained from American Type Culture Collection (Manassas, Va.), were cultured at 37° C. in 5% CO2 using DMEM containing 10% FBS and antibiotics (100 U/ml of penicillin, and 100 µg/ml streptomycin). Cells (1×10$^6$/ml) were incubated with peptide (10 µg/ml) in a volume of 2 ml. After 8 h of cultures cells were washed and prepared for nuclear extracts.

Nuclear extracts and EMSA were prepared according to Schreiber et al. Methods (Schreiber et al. 1989, Nucleic Acids Research 17). Briefly, nuclear extracts from peptide stimulated or nonstimulated macrophages were prepared by cell lysis followed by nuclear lysis. Cells were then suspended in 400 µl of buffer (10 mM HEPES (pH 7.9), 10 mM KCl, 0.1 mM KCl, 0.1 mM EDTA, 0.1 mM EGTA, 1 mM DTT, 0.5 mM PMSF and protease inhibitors), vigorously vortexed for 15 s, left standing at 4° C. for 15 min, and centrifuged at 15,000 rpm for 2 minutes. The pelleted nuclei were resuspended in buffer (20 mM HEPES (pH 7.9), 10% glycerol, 400 mM NaCl, 1 mM EDTA, 1 mM EGTA, 1 mM DTT, 0.5 mM PMSF and protease inhibitors) for 30 minutes on ice, then the lysates were centrifuged at 15,000 rpm for 2 minutes. The supernatants containing the solubilized nuclear proteins were stored at −70° C. until used for the Electrophoretic Mobility Shift Assays (EMSA).

Electrophoretic mobility shift assays were performed by incubating nuclear extracts prepared from control (RAW 264.7) and peptide treated RAW 264.7 cells with a 32P-labeled double-stranded probe (5' AGCTCAGAGGGG-GACTTTCCGAGAG 3') (SEQ ID NO: 28) synthesized to represent the NF-κB binding sequence. Shortly, the probe was end-labeled with T4 polynucleotide kinase according to manufacturer's instructions (Promega, Madison, Wis.). The annealed probe was incubated with nuclear extract as follows: in EMSA, binding reaction mixtures (20 µl) contained 0.25 µg of poly(dI-dC) (Amersham Pharmacia Biotech) and 20,000 rpm of 32P-labeled DNA probe in binding buffer consisting of 5 mM EDTA, 20% Ficoll, 5 mM DTT, 300 mM KCl and 50 mM HEPES. The binding reaction was started by the addition of cell extracts (10 µg) and was continued for 30 min at room temperature. The DNA-protein complex was resolved from free oligonucleotide by electrophoresis in a 6% polyacrylamide gel. The gels were dried and exposed to x-ray films.

The transcription factor NF-κB participates in the transcriptional regulation of a variety of genes. Nuclear protein extracts were prepared from LPS and peptide treated RAW264.7 cells or from LPS treated RAW264.7 cells. In order to determine whether the peptide modulates the translocation of NF-κB into the nucleus, on these extracts EMSA was performed. Here we see that indeed some peptides are able to modulate the translocation of NF-κB since the amount of labeled oligonucleotide for NF-κB is reduced. In this experiment peptides that show the modulation of translocation of NF-κB are: VLPALPQVVC (SEQ ID NO: 21, LQGV-LPALPQ (SEQ ID NO: 22), LQG, LQGV (SEQ ID NO: 1), GVLPALPQ (SEQ ID NO: 23), VLPALP (SEQ ID NO: 4), VLPALPQ (SEQ ID NO: 13), GVLPALP (SEQ ID NO: 16, VVC, MTRV (SEQ ID NO: 20), MTR.

RAW 264.7 mouse macrophages were cultured in DMEM, containing 10% or 2% FCS, penicillin, streptomycin and glutamine, at 37° C., 5% CO$_2$. Cells were seeded in a 12-wells plate (3×10$^6$ cells/ml) in a total volume of 1 ml for 2 hours and then stimulated with LPS (*E. coli* 026:B6; Difco Laboratories, Detroit, Mich.) and/or NMPF (1 microgram/ml). After 30 minutes of incubation plates were centrifuged and cells were collected for nuclear extracts. Nuclear extracts and EMSA were prepared according to Schreiber et al. Cells were collected in a tube and centrifuged for 5 minutes at 2000 rpm (rounds per minute) at 4° C. (Universal 30 RF, Hettich Zentrifuges). The pellet was washed with ice-cold Tris.buffered saline (TBS pH 7.4) and resuspended in 400 µl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche) and left on ice for 15 minutes. Twenty five micro liter 10% NP-40 was added and the sample was centrifuged (2 minutes, 4000 rpm, 4° C.). The supernatant (cytoplasmic fraction) was collected and stored at −70° C. The pellet, which contains the nuclei, was washed with 50 µl buffer A and resuspended in 50 µl buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples were left to shake at 4° C. for at least 60 minutes. Finally the samples were centrifuged and the supernatant (nucleic fraction) was stored at −70° C.

Bradford reagent (Sigma) was used to determine the final protein concentration in the extracts. For electrophoretic mobility shift assays (EMSA) an oligonucleotide representing NF-κB binding sequence (5'-AGC TCA GAG GGG GAC TTT CCG AGA G-3') (SEQ ID NO: 28) was synthesized. Hundred pico mol sense and antisense oligo were annealed and labeled with γ-$^{32}$P-dATP using T4 polynucleotide kinase according to manufacturer's instructions (Promega, Madison, Wis.). Nuclear extract (5-7.5 µg) was incubated for 30 minutes with 75000 cpm probe in binding reaction mixture (20 microliter) containing 0.5 µg poly dI-dC (Amersham Pharmacia Biotech) and binding buffer BSB (25 mM $MgCl_2$, 5 mM $CaCl_2$, 5 mM DTT and 20% Ficoll) at room temperature. The DNA-protein complex was resolved from free oligonucleotide by electrophoresis in a 4-6% polyacrylamide gel (150 V, 2-4 hours). The gel was then dried and exposed to x-ray film. The transcription factor NF-κB participates in the transcriptional regulation of a variety of genes. Nuclear protein extracts were prepared from either LPS (1 mg/ml), peptide (1 mg/ml) or LPS in combination with peptide treated and untreated RAW264.7 cells. In order to determine whether the peptides modulate the translocation of NF-κB into the nucleus, on these extracts EMSA was performed. Peptides are able to modulate the basal as well as LPS induced levels of NF-κB. In this experiment peptides that show the inhibition of LPS induced translocation of NF-κB are: VLPALPQVVC (SEQ ID NO: 21), LQGVLPALPQ (SEQ ID NO: 22, LQG, LQGV (SEQ ID NO: 1), GVLPALPQ (SEQ ID NO: 23), VLPALP (SEQ ID NO: 4), VVC, MTR and circular LQGVLPALPQVVC (SEQ ID NO: 17). Peptides that in this experiment promote LPS induced translocation of NF-κB are: VLPALPQ (SEQ ID NO: 13), GVLPALP (SEQ ID NO: 16) and MTRV (SEQ ID NO: 20). Basal levels of NF-κB in the nucleus was decreased by VLPALPQVVC (SEQ ID NO: 21), LQGVLPALPQ (SEQ ID NO: 22), LQG and LQGV (SEQ ID NO: 1) while basal levels of NF-κB in the nucleus was increased by GVLPALPQ (SEQ ID NO: 23), VLPALPQ (SEQ ID NO: 13), GVLPALP (SEQ ID NO: 16), VVC, MTRV (SEQ ID NO: 20), MTR and LQGVLPALPQVVC (SEQ ID NO: 17). In other experiments, QVVC also modulated the translocation of NF-κB into the nucleus (data not shown).

Further modes of identification of gene-regulatory peptides by NFκB analysis

Cells: Cells will be cultured in appropriate culture medium at 37° C., 5% $CO_2$. Cells will be seeded in a 12-wells plate (usually 1×10$^6$ cells/ml) in a total volume of 1 ml for 2 hours and then stimulated with regulatory peptide in the presence or absence of additional stimuli such as LPS. After 30 minutes of incubation plates will be centrifuged and cells are collected for cytosolic or nuclear extracts.

Nuclear Extracts: Nuclear extracts and EMSA could be prepared according to Schreiber et al. Method (Schreiber et al. 1989, Nucleic Acids Research 17). Cells are collected in a tube and centrifuged for 5 minutes at 2000 rpm (rounds per minute) at 4° C. (Universal 30 RF, Hettich Zentrifuges). The pellet is washed with ice-cold Tris buffered saline (TBS pH 7.4) and resuspended in 400 µl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche) and left on ice for 15 minutes. Twenty five micro liter 10% NP-40 is added and the sample is centrifuged (2 minutes, 4000 rpm, 4° C.). The supernatant (cytoplasmic fraction) was collected and stored at −70° C. for analysis. The pellet, which contains the nuclei, is washed with 50 µl buffer A and resuspended in 50 µl buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples are left to shake at 4° C. for at least 60 minutes. Finally the samples are centrifuged and the supernatant (nucleic fraction) is stored at −70° C. for analysis.

Bradford reagent (Sigma) could be used to determine the final protein concentration in the extracts.

EMSA: For Electrophoretic mobility shift assays an oligonucleotide representing NF-κB binding sequence such as (5'-AGC TCA GAG GGG GAC TTT CCG AGA G-3') (SEQ ID NO: 28) are synthesized. Hundred pico mol sense and antisense oligo are annealed and labeled with γ-$^{32}$P-dATP using T4 polynucleotide kinase according to manufacture's instructions (Promega, Madison, Wis.). Cytosolic extract or nuclear extract (5-7.5 µg) from cells treated with regulatory peptide or from untreated cells is incubated for 30 minutes with 75000 cpm probe in binding reaction mixture (20 µl) containing 0.5 µg poly dI-dC (Amersham Pharmacia Biotech) and binding buffer BSB (25 mM $MgCl_2$, 5 mM $CaCl_2$, 5 mM DTT and 20% Ficoll) at room temperature. Or cytosolic and nuclear extract from untreated cells or from cells treated with stimuli could also be incubated with probe in binding reaction mixture and binding buffer. The DNA-protein complex is resolved from free oligonucleotide by electrophoresis in a 4-6% polyacrylamide gel (150 V, 2-4 hours). The gel is then dried and exposed to x-ray film. Peptides can be biotinylated and incubated with cells. Cells are then washed with phosphate-buffered saline, harvested in the absence or presence of certain stimulus (LPS, PHA, TPA, anti-CD3, VEGF, TSST-1, VIP or know drugs etc.). After culturing cells are lysed and cells lysates (whole lysate, cytosolic fraction or nuclear fraction) containing 200 micro gram of protein are incubated with 50 miroliter Neutr-Avidin-plus beads for 1 h at 4° C. with constant shaking. Beads are washed five times with lysis buffer by centrifugation at 6000 rpm for 1 min. Proteins are eluted by incubating the beads in 0.05 N NaOH for 1 min at room temperature to hydrolyze the protein-peptide linkage and analyzed by SDS-polyacrylamide gel electrophoresis followed by immunoprecipitated with agarose-conjugated anti-NF-κB subunits antibody or immunoprecipitated with antibody against to be studied target. After hydrolyzing the protein-peptide linkage, the sample could be analyzed on HPLS and mass-spectrometry. Purified NF-κB subunits or cell lysate interaction with biotinylated regulatory peptide can be analyzed on biosensor technology. Peptides can be labeled with FITC and incubated with cells in the absence or presence of different stimulus. After culturing, cells can be analyzed with fluorescent microscopy, confocal microscopy; flow cytometry (cell membrane staining and/or intracellular staining) or cells lysates are made and analyzed on HPLC and mass-spectrometry. NF-κB transfected (reporter gene assay) cells and gene array technology can be used to determine the regulatory effects of peptides.

HPLC and mass-spectrometry analysis: Purified NF-κB subunit or cytosolic/nuclear extract is incubated in the absence or presence of (regulatory) peptide is diluted (2:1) with 8 N guanidinium chloride and 0.1% trifluoroacetic acid, injected into a reverse-phase HPLC column (Vydac C18) equilibrated with solvent A (0.1% trifluoroacetic acid), and eluted with a gradient of 0 to 100% eluant B (90% acetonitrile in solvent A). Factions containing NF-κB subunit are pooled and concentrated. Fractions are then dissolved in appropriate volume and could be analyzed on mass-spectrometry.

Further references:

PCT International Publications WO99/59617, WO01/72831, WO97/49721, WO01/10907, and WO01/11048, the contents of the entirety of all of which are incorporated by this reference.

What is claimed is:

1. A method of treating a subject suffering from multiple sclerosis (MS) and presenting clinical signs of MS exacerbations, said method comprising:
   administering to the subject an isolated peptide consisting of LQGV (SEQ ID NO: 1) in an amount effective to decrease NFκB-mediated pro-inflammatory cytokine release, so as to treat the subject suffering from multiple sclerosis and presenting clinical signs of MS exacerbations.

* * * * *

```
                          SEQUENCE LISTING

<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Gln Gly Val
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Gln Gly Val
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Gln Gly Ala
  1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Leu Pro Ala Leu Pro
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Leu Pro Ala Leu Pro
  1               5
```

```
<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ala Pro Ala Leu Pro
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Leu Pro Ala Leu Pro Gln
 1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Pro Ala Ala Pro Gln
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Leu Pro Ala Leu Ala Gln
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Ala Gly Val
 1

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

```
Val Leu Ala Ala Leu Pro
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Leu Pro Ala Leu Ala
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Leu Pro Ala Leu Pro Gln
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Leu Ala Ala Leu Pro Gln
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Leu Pro Ala Leu Pro Ala
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Val Leu Pro Ala Leu Pro
 1               5

<210> SEQ ID NO 17
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 17

Leu Gln Gly Val Leu Pro Ala Leu Pro Gln Val Val Cys
 1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Pro Gly Cys Pro Arg Gly Val Asn Pro Val Val Ser
 1               5                  10

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Gly Cys
 1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Thr Arg Val
 1

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Leu Pro Ala Leu Pro Gln Val Val Cys
 1               5                  10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Gln Gly Val Leu Pro Ala Leu Pro Gln
 1               5                  10
```

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Val Leu Pro Ala Leu Pro Gln
 1               5

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Val Cys Asn Tyr Arg Asp Val Arg Phe Glu Ser Ile Arg Leu Pro
 1               5                  10                  15

Gly Cys Pro Arg Gly Val Asn Pro Val Val Ser Tyr Ala Val Ala Leu
            20                  25                  30

Ser Cys Gln Cys Ala Leu
        35

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Pro Arg Cys Arg Pro Ile Asn Ala Thr Leu Ala Val Glu Lys Glu
 1               5                  10                  15

Gly Cys Pro Val Cys Ile Thr Val Asn Thr Thr Ile Cys Ala Gly Tyr
            20                  25                  30

Cys Pro Thr
        35

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Lys Ala Pro Pro Pro Ser Leu Pro Ser Pro Ser Arg Leu Pro Gly
 1               5                  10                  15

Pro Ser

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 27

Ser Ile Arg Leu Pro Gly Cys Pro Arg Gly Val Asn Pro Val Val Ser
  1               5                  10                  15

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
agctcagagg gggactttcc gagag                                         25

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Val Val Cys
  1
```